US00PP11655P

United States Patent [19]

Vlielander

[11] Patent Number: Plant 11,655

[45] Date of Patent: Nov. 28, 2000

[54] KALANCHOE PLANT NAMED 'LTPINK KIEBESSY II'

[75] Inventor: Ike Vlielander, De Lier, Netherlands

[73] Assignee: Fides Beheer B.V., De Lier, Netherlands

[21] Appl. No.: 09/233,129

[22] Filed: Jan. 19, 1999

[51] Int. Cl.[7] ..... A01H 5/00

[52] U.S. Cl. ..... Plt./339

[58] Field of Search ..... Plt./339, 335, 337, Plt./341

[56] References Cited

U.S. PATENT DOCUMENTS

| | | | |
|---|---|---|---|
| P.P. 5,876 | 2/1987 | Mikkelsen | Plt./339 |
| P.P. 5,889 | 2/1987 | Finger | Plt./339 |
| P.P. 7,286 | 7/1990 | Drewlow | Plt./339 |
| P.P. 10,268 | 3/1998 | Jepsen | Plt./337 |

*Primary Examiner*—Howard J. Locker
*Assistant Examiner*—Kent L. Bell
*Attorney, Agent, or Firm*—C. A. Whealy

[57] ABSTRACT

A distinct cultivar of Kalanchoe plant named 'LtPink Kiebessy II', characterized by its light pink petal color; vigourous plant growth habit; rapid growth rate; freely branching habit with shoots forming at every node; dark green leaves; proportional leaf size to plant size; suitable for various container sizes from 10 to 12 cm; uniform plant habit and inflorescence display; freely flowering with numerous flowers per plant; and excellent postproduction longevity with plants maintaining good flower color and substance for about five to seven weeks.

1 Drawing Sheet

BACKGROUND OF THE INVENTION

The present invention relates to a new and distinct cultivar of Kalanchoe plant, botanically known as *Kalanchoe blossfeldiana* Adans., and hereinafter referred to by the cultivar name 'LtPink Kiebessy II'.

The new Kalanchoe is naturally-occurring whole plant mutation of the *Kalanchoe blossfeldiana* Adans. cultivar 'Kiebessy', disclosed in U.S. Plant Pat. No. 7,767. The new Kalanchoe was discovered by the Inventor in a controlled environment in De Lier, The Netherlands, within a population of plants of the cultivar Kiebessy. The selection of this plant was based on its lighter pink petal color.

Asexual reproduction of the new Kalanchoe by terminal cuttings taken at De Lier, The Netherlands, has shown that the unique features of this new Kalanchoe are stable and reproduced true to type in successive generations.

BRIEF SUMMARY OF THE INVENTION

Plants of the cultivar 'LtPink Kiebessy II' have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'LtPink Kiebessy II'. These characteristics in combination distinguish 'LtPink Kiebessy II' as a new and distinct cultivar:

1. Light pink petal color.
2. Vigorous plant growth habit.
3. Rapid growth rate.
4. Freely branching habit with shoots forming at every node. Plants do not require pinching.
5. Dark green leaves.
6. Proportional leaf size to plant size.
7. Suitable for various container sizes from 10 to 12 cm.
8. Uniform plant habit and inflorescence display.
9. Freely flowering with numerous flowers per plant.

10. Excellent postproduction longevity with plants maintaining good flower color and substance for about five to seven weeks.

Plants of the cultivar 'LtPink Kiebessy II' are similar to plants of the mutation parent, the cultivar 'Kiebessy', in many characteristics. However in side-by-side comparisons conducted by the Inventor in De Lier, The Netherlands, plants of the new Kalanchoe differ from plants of the cultivar 'Kiebessy' in the following characteristics:

1. Plants of the new Kalanchoe are slightly taller than plants of the cultivar 'Kiebessy'.
2. Plants of the Kalanchoe have fewer and smaller leaves than plants of the cultivar 'Kiebessy'.
3. Plants of the new Kalanchoe have lighter pink petal color than plants of the cultivar 'Kiebessy'.

DESCRIPTION OF THE PHOTOGRAPH

The accompanying colored photograph illustrates the overall appearance of the new Kalanchoe, showing the colors as true as it is reasonably possible to obtain in colored reproductions of this type. The photograph comprises a top perspective view of a typical potted plant of 'LtPink Kiebessy II' taken under natural light conditions at approximately noon in De Lier, The Netherlands. Flower and foliage colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations, measurements and comparisons describe plants grown in De Lier, The Netherlands, from December to April under commercial practice in a glass-covered greenhouse with day temperatures ranging from 19 to 21° C. and night temperatures of 18 to 19° C. Light levels were maintained between 10,000 to 55,000 lux using assimilation lights and shading. Plants were exposed to four weeks of long day/short nights followed by eight weeks of short day/long night photoperiodic treatments and treated with daminozide growth retardant at a rate of 4 grams per liter. Measurements and numerical values represent averages for typical plants grown in 10.5-cm containers.

Botanical classification: *Kalanchoe blossfeldiana* Adans. cultivar 'LtPink Kiebessy II'.

Parentage: Naturally-occurring whole plant mutation of *Kalanchoe blossfeldiana* Adans. cultivar 'Kiebessy', disclosed in U.S. Plant Pat. No. 7,767.

Propagation:

*Type cutting*.—Terminal cuttings.

*Time to initate roots*.—12 days at 21° C. soil temperature.

*Rooting habit*.—Numerous, fine, fibrous, and well-branched.

Plant description:

*Form*.—Upright and uniform. Plant shape is an inverted triangle with a rounded apex. Actual plant shape will depend on whether or not plants are pinched (vegetative terminals removed).

*Branching habit*.—Freely branching, generally shoots formed at every node. Typically 6 to 7 lateral branches will develop.

*Plant height at flowering*.—About 23 cm from soil level to top of plant, appropriate for 10 to 12-cm containers.

*Lateral branch length*.—About 20 cm.

*Vigor*.—Vigorous.

*Growth rate*.—Rapid.

*Crop time*.—Depending on temperature and light level, three to four weeks of long day/short night conditions followed by 7.5 to 11 weeks of short day/long night conditions for a total of 10.5 to 15 weeks are required to produce flowering plants with four to seven open flowers per plant.

*Foliage description*.—Leaves simple, opposite, generally symmetrical. Quantity: Typically about 11 to 16 mature leaves and about 14 to 22 generative leaves per plant. Length: About 12 cm. Width: About 9 cm. Petiole length: About 1.6 cm. Shape: Elliptic. Apex: Acute to obtuse. Base: Acute. Margin: Crenate. Texture: Leathery, glabrous, coriaceous and succulent. A wart-like structure is typically observed on the upper leaf surface close to the leaf base. Color: Young foliage, upper surface: 137A. Young foliage, lower surface: 137C. Mature foliage, upper surface: 147A. Mature foliage, lower surface: 147B. Petiole: 137A. Venation, upper surface: 147A to 147B. Venation, lower surface: 147B.

Flower description:

*Flower type and habit*.—Single flowers arranged in compound dichasial cymes on strong peduncles. Inflorescences borne above the foliage, arising from leaf axils. Uniform inflorescence display. Freely flowering and very floriferous.

*Natural flowering season*.—Autumn/winter in the Northern Hemisphere. At other times of the year flower initiation and development can be induced under controlled photoperiods (short day/long night conditions). Opening of new buds will continue for at least seven weeks.

*Time to flower*.—Under warm growing temperatures, about 25° C., plants of the new Kalanchoe will flower after about 7.5 weeks of exposure to controlled photoperiods (short day/long night conditions). Under cooler growing temperatures, about 20° C., plants of the cultivar 'LtPint Kiebessy II' will flower after about 11 weeks of exposure to controlled photoperiods. First flower open is the terminal flower at the main axis and is followed by the opening of the terminal flowers of the lateral branches of the inflorescence.

*Postproduction longivity*.—Plants will maintain good color and substance for about five to seven weeks depending on environmental conditions. Individual flowers last about 24 days after opening. Flowers persistent.

*Fragrance*.—None.

*Flower diameter*.—About 1.6 cm.

*Flower depth (height)*.—About 1.3 cm.

*Quantity*.—Typically more than 200 flowers per plant.

*Flower buds*.—Length: About 1 cm. Width: About 2.5 mm. Shape: Oblong becoming tubular/ovoid with development. Rate of opening: Relatively rapid. Color: Sepals, initially 138C; petals, 49D just before opening.

*Petals*.—Quantity: Four forming a bell-shaped corolla. Length: About 7 mm. Width: About 4.5 mm. Shape: Ovate. Apex: Acute. Margin: Entire. Texture: Glabrous, smooth, shiny and satiny. Aspect: Flat to somewhat upright. Color: When opening: 68B. Mature, upper surface: 68B. Mature, lower surface: 55B to 55D. Fading to: 68C to 68D.

*Sepals*.—Quantity: Four. Shape: Oblong, pointed. Apex: Acute. Margin: Entire. Texture: Glabrous and shiny. Aspect: Upright, rigid. Color, upper and lower surfaces: 138D.

*Calyx*.—Size: About 9 mm. Shape: Funnel. Texture: Glabrous. Color: 138D.

*Peduncle*.—Length: About 5 mm. Texture: Glabrous. Aspect: Strong, rigid, and upright. Color: 138B.

*Reproductive organs*.—Stamens: Stamen number: Eight. Anther size: About 0.3 mm. Anther shape: Flat, elliptic. Anther color: Close to 150D. Pollen color: Close to 12A. Pistils: Pistil number: Four. Stigma shape: Flat. Stigma appearance: Crystalline. Stigma color: 8D. Style length: About 8 mm. Style color: 138D. Ovary number: Four-celled. Ovary color: Green.

Disease resistance: Resistance to known Kalanchoe pathogens has not been observed.

Seed production: Seed production has not been observed.

I claim

1. A new and distinct cultivar of Kalanchoe plant named 'LtPink Kiebessy II', as illustrated and described.

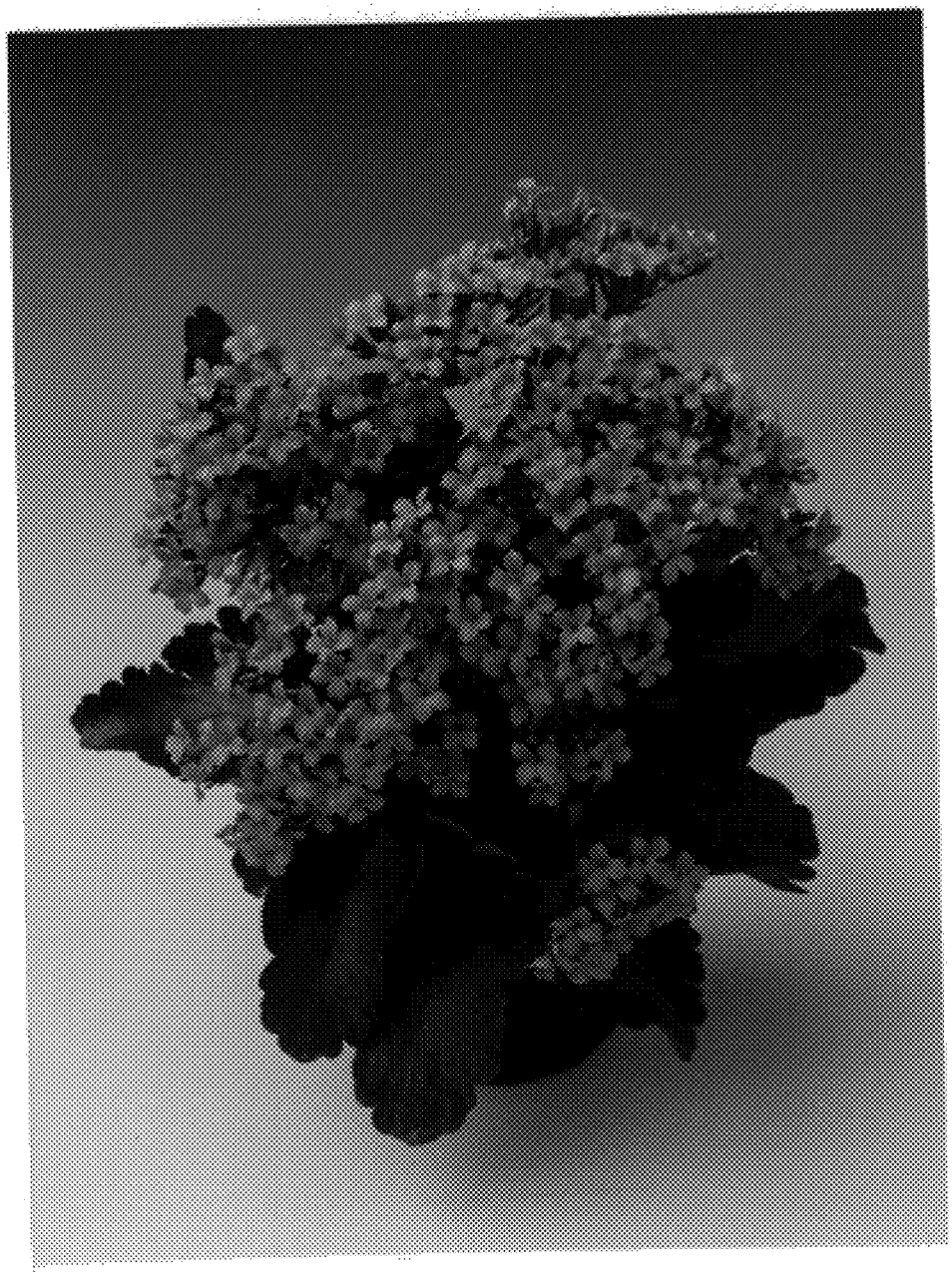

* * * * *